United States Patent [19]

Willingham et al.

[11] Patent Number: 5,320,956
[45] Date of Patent: Jun. 14, 1994

[54] MONOCLONAL ANTIBODY USEFUL FOR THE DIAGNOSIS OF CANCER

[75] Inventors: Mark C. Willingham, Bethesda; Kai Chang, Silver Spring; Ira Pastan, Potomac, all of Md.

[73] Assignee: The United States of America as represented by the Department of Health and Human Services, Washington, D.C.

[21] Appl. No.: 977,727

[22] Filed: Nov. 16, 1992

Related U.S. Application Data

[63] Continuation of Ser. No. 596,291, Oct. 12, 1990, abandoned.

[51] Int. Cl.$^5$ .................. A61K 35/00; A61K 35/16; C07K 15/28
[52] U.S. Cl. .................. 435/172.2; 424/85.8; 435/240.27; 530/388.8
[58] Field of Search .................. 435/172.2, 240.27; 424/85.8; 530/388.8

[56] References Cited

PUBLICATIONS

Waldmann Science 252:1657–1662 1991.
Blattler Cancer Cells 1(2):50–55 1989.
Riechmann et al. Nature 332:323–327 1988.
Abramowicz et al. New Eng J Med. Sep. 3, 1992 p. 736.
Blast et al. J Clin Invest 68: 1331–1337 '81.
Hamilton et al. Cancer Research 43:5379–5389 '83.

*Primary Examiner*—David L. Lacey
*Assistant Examiner*—Donato E. Adams
*Attorney, Agent, or Firm*—Townsend and Townsend Khourie and Crew

[57] ABSTRACT

The invention provides novel monoclonal antibodies and the hybridomas that secrete them. The antibodies can be used for the diagnosis of a number of cancers, such as ovarian, esophageal and cervical carcinomas. A preferred antibody is secreted by a hybridoma deposited with the ATCC and has Accession No. HB 10570.

13 Claims, 1 Drawing Sheet

MONOCLONAL ANTIBODY USEFUL FOR THE DIAGNOSIS OF CANCER

This is a continuation of application Ser. No. 07/596,291 filed Oct. 12, 1990, now abandoned.

BACKGROUND OF THE INVENTION

1. Technical Field

The subject invention relates to a monoclonal antibody, referred to as K1, and uses thereof.

In particular, the K1 monoclonal antibody can be used in the treatment and diagnosis of several forms of cancer.

2. Background Information

Current therapies for metastatic human cancers, such as radiation or chemotherapy, center on agents that selectively kill rapidly growing cancer cells. Unfortunately, many tumors do not show an unusually fast growth rate compared to important normal tissues, such as bone marrow or the epithelium of the gastrointestinal tract. An alternative group of therapeutic approaches targets unique chemical structures on the surface of tumor cells for therapy, most often employing antibodies that bind selectively to these target molecules. One of these therapeutic approaches employs antibodies that are coupled to cell-killing agents, such as plant or bacterial toxins. These antibody-toxin complexes, or immunotoxins, have been shown to be capable of selectively killing tumor cells in model tumor systems in tissue culture and in laboratory animals (Pastan et al., Cell 47:641–648 (1986)).

In spite of many attempts to isolate such tumor-specific antibodies for human therapy, there are still very few antibodies identified that selectively bind only to tumor cells and not to other important normal tissues. Isolation of such tumor-specific antibodies is, therefore, of importance for the application of such immuno-directed therapies.

Monoclonal antibody methodology as originally described by Kohler and Milstein (Nature 156:495–497 (1975) and disclosed in Koprowski et al. (U.S. Pat. No. 4,172,124) has allowed the isolation of antibodies in pure form for the construction of therapeutic agents. However, two problems have prevented the application of many previously isolated antibodies. First, many monoclonal antibodies reactive with tumor cells also react with important normal human tissues. Secondly, many of the isolated antibodies bind to surface elements that do not efficiently mediate the entry of toxin conjugates into cells by endocytosis. The present invention relates to a monoclonal antibody, K1, that selectively binds to some human tumors, but not to many important normal tissues. This antibody, when incorporated as the targeting element of an immunotoxin, also has been shown to allow efficient entry of these toxic agents into cells.

An antibody reactive with an antigen shed into the plasma of patients with ovarian cancer has previously been isolated. This antibody, OC125, reactive with this shed antigen, CA125, has been employed in diagnosis of primary and recurrent ovarian cancer (Bast et al., J. Clin. Invest. 68: 1331 (1981)). However, evidence indicates that the K1 monoclonal antibody recognizes an epitope on the cell surface which is entirely different from the one recognized by OC125. Furthermore the antigen which reacts with K1 is not shed into plasma of patients with ovarian cancer. The lack of shedding into plasma makes K1 a much better candidate antibody for immunotherapy, since it would not be neutralized by circulating antigen immediately upon injection into the blood stream.

All U.S. patents and publications referred to herein are hereby incorporated by reference.

SUMMARY OF THE INVENTION

The subject invention relates to a monoclonal antibody, referred to as K1, and to the uses thereof.

In particular, the antibody can be used as a therapeutic targeting agent in the treatment and diagnosis of several forms of cancers.

More specifically, the present invention relates to a hybridoma which produces a monoclonal antibody specific for a cell surface antigen wherein said antigen is characterized by expression on normal primate tissue, malignant human cultured cell lines and human tumor, and is not shed into culture media or plasma. The hybridoma cell line has the accession number ATCC HB 10570 and was deposited at the American Type Culture Collection in Rockville, Md.

The invention particularly relates to the monoclonal antibody itself which is specific for a cell surface antigen having the above properties, and which is produced by the hybridoma. The monoclonal antibody is of the IgG class.

The human cultured cell line referred to above is selected from the group consisting of, for example, OVCAR-2, OVCAR-3, OVCAR-4, 1847, HTB77, HeLa S3, KB, AGS and HTB103. The normal primate tissue which expresses the antigen is, for example, mesothelium. The human tumor is derived from, for example, an ovarian carcinoma, an esophageal carcinoma or a cervical carcinoma.

The present invention also includes a method of treating cancer comprising administering to a patient in need of said treatment an amount of a conjugate of the monoclonal antibody sufficient to effect said treatment. The type of cancer treated may be, for example, ovarian cancer. The antibody is conjugated with, for example, a toxin, radionuclide, or chemotherapeutic agent. The antibody may also be modified to mediate cell killing.

Moreover, the present invention also includes a method of diagnosing cancer in a patient comprising administering to said patient an amount of the monoclonal antibody sufficient to effect said diagnosis. The monoclonal antibody may be radioactively labelled. The diagnosis may be made by visualizing the presence of the radiolabel.

The present invention also includes a pharmaceutical composition comprising the monoclonal antibody in a concentration sufficient to inhibit tumor growth, together with a pharmaceutically acceptable carrier.

Furthermore, the invention also includes a method of diagnosing cancer in a patient comprising the steps of
removing a tissue or fluid sample from said patient;
adding the monoclonal antibody to said sample; and
visualizing the presence of the antibody in said sample.

Figure 1:
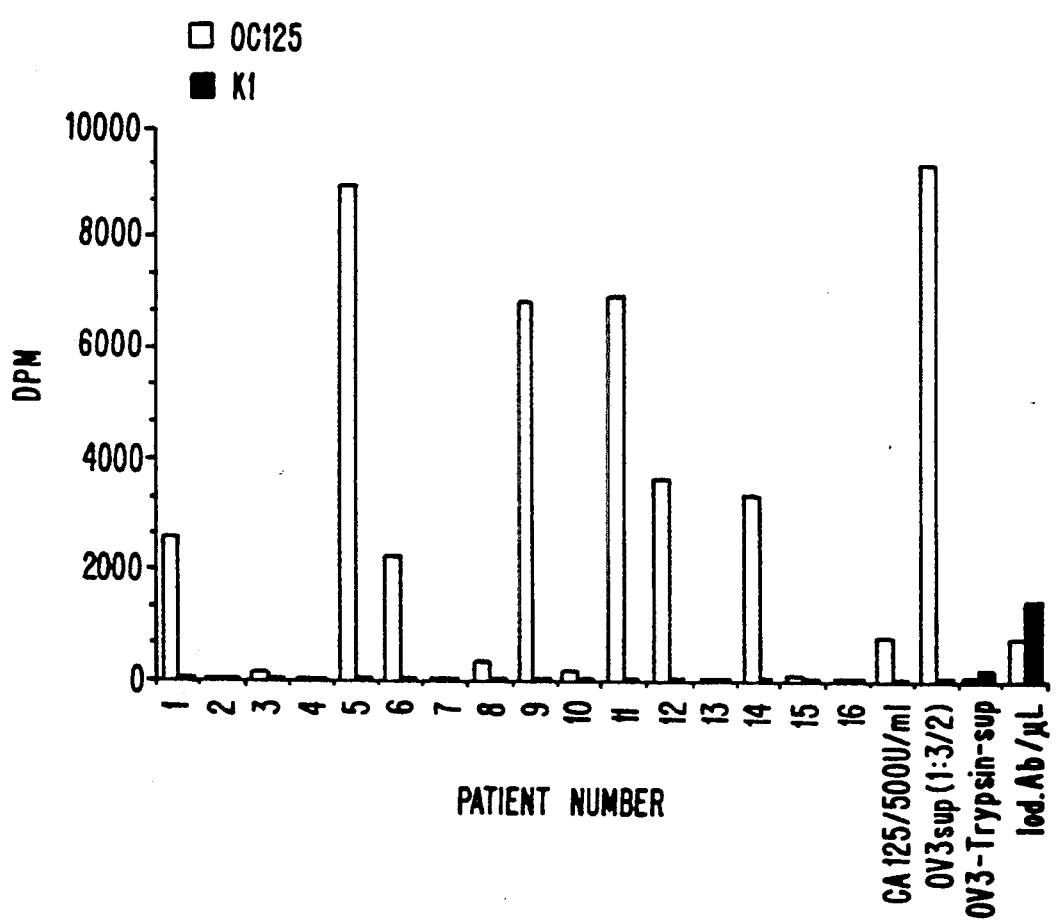
FIG. 1 represents the results of a radiolabeled antibody assay of serum samples from patients with ovarian cancer.

K1 or OC125 was attached to microtiter wells, and samples of patient sera or culture supernatant were added using a procedure similar to that shown in Table VIII. The wells were then incubated with either iodinated radioactive K1 in wells pre-treated with K1 (K1 system) or radioactive OC125 in wells pre-treated with Oc125 unlabeled antibody (OC125 system). Analogous to Table VIII, supernatant from OVCAR-3 cultures (concentrate diluted 1:3, value divided by 2) showed binding of OC125 detected by labeled OC125 antibody. In contrast, such supernatants incubated with bound K1, then detected with iodinated K1 antibody, show no detectable signal. A CA125 purified antigen standard sample shows reaction with the OC125 system, but not with the K1 system. Samples of patient sera show variable levels of signal with the OC125 system, but no signa, with the K1 system. The K1 system detects a weak signal in the trypsinate of OVCAR-3 cells, where the OC125 antigen is destroyed by trypsin treatment, and shows no signal with the OC125 system. An aliquot of both labeled antibodies shows levels of radioactivity sufficient to allow adequate sensitivity.

DETAILED DESCRIPTION OF THE INVENTION

One manner of generating the K1 monoclonal antibody of the present invention involves immunizing a mouse, for example, with periodate-treated human ovarian carcinoma cells, and then isolating the spleen cells of the mouse which are reactive with the immunizing ovarian cancer cells. Such reactive spleen cells are then fused with AG8 mouse myeloma cells in order to create hybridomas or clones. Clones are then selected based on their ability to react with the immunizing cells. A secondary screening procedure can then be undertaken in which the clones are exposed to ovarian tumors and normal tissues. In the present case, the clones should be highly reactive with the carcinomas and non-reactive with normal human tissues. Antibody may then be obtained from the clones by ascites production in mice or by harvesting culture supernatants of the clones. The antibody may then be purified.

In order to determine the potential usefulness of the antibody, with respect to cancer treatment and diagnosis, one must establish the location(s) and distribution of the epitope which reacts with the antibody. Normal human tissues and tumors as well as normal Cynomologous monkey tissues can be utilized for this purpose.

The distribution of reactivity or location of the epitope which is reactive with the K1 antibody is shown in Table I below. In particular, Table I establishes that the K1-reactive epitope is present in the serosa in the mesothelial cells of the peritoneum, pericardium and pleura, as well as in a limited distribution in the tracheal epithelium, tonsillar epithelium and epithelium of the Fallopian tube.

TABLE I

Immunohistochemical Localization of K1 and OC125 in Normal Human and Monkey Tissues

| | K1 | OC125 |
|---|---|---|
| Normal Human Tissues | | |
| Liver | (−)(3/3) | (−)(3/3) |
| Kidney | (−)(3/3) | (−)(3/3) |
| Cardiac Muscle | (−)(6/6) | (−)(6/6) |
| | (++ pericardium) | (++ pericardium) |
| Lung | (−)(1/1) | (−)(1/1) |
| | (++ pleural mesothelium | (++ pl. mesothelium (+ ap. bronchi) |
| Cerebral Cortex | (−)(1/1) | (−)(1/1) |
| Cerebellum | (−)(2/2) | (−)(1/1) |
| Spinal cord | (−)(2/2) | ((−, except ?het minor cell pop.)(2/2) |
| Pituitary | (−)(1/1) | (−)(1/1) |
| Bone Marrow | (−)(1/1) | (−)(1/1) |
| Adrenal | (−)(1/1) | (−)(1/1) |
| Spleen | (−)(1/1) | nd |
| Lymph Node | (−)(1/1) | (−)(1/1) |
| Skin | (−) <2.5 μg/ml (2/2) | (−)(2/2) |
| Skeletal | (−)(1/1) | (−)(1/1) |
| Peripheral Nerve | (−)(1/1) | (−)(1/1) |
| Tonsil | (++ het epith.) (2/2) | (++ het epith.) (2/2) |
| Esophagus | (−)(2/2) | (−)(1/1) |
| Small Bowel | (−epith)(3/3) (++ serosa) | (−epith)(4/4) (++ serosa)(2/2) |
| Stomach | (−)(2/2) | (−)(1/1) |
| Normal Colon | (−)(2/2) | (−)(1/1) |
| Bladder | (−)(3/3) | (−)(3/3) |
| Pancreas | (−)(2/2) | (−)(2/2)(het + acini)(1/1) |
| Salivary Gland | (−)(1/1) | (het + acini)(1/1); (++ het ducts)(1/2) |
| Mammary Gland | (−)(1/1) | (−)(1/1) |
| Fallopian Tube | (++ epith)(1/1) | (++ epith)(1/1) |
| Epididymis | (−)(1/1) | nd |
| Thyroid | (−)(2/2) | (−)(2/2) |
| Parathyroid | (−)(1/1) | (−)(1/1) |
| Ovary | (++ serosal epith) (2/2) | (−, het + serosal epith)(2/2) |
| Testis | (−)(1/1)(− tunica) | (−)(except occ + cells in tunica)(1/1) |
| Prostate | (−)(2/2 | (−)(2/2) |
| Uterus | (−endom.)(1) | (++ apic. endom.) (1/1);(++serosa)(2/2) |
| Trachea | (++basal epith.)(1/1) | (++ apical epith.) (1/1) |
| Gall Bladder | (−)(1/1) | (−)(1/1) |
| Normal Cynomologous Monkey Tissues | | |
| Liver | (−)(1/1) | (−)(1/1) |
| Kidney | (−)(1/1) | (−)(1/1) |
| Heart | (−)(1/1) | (−)(1/1) |
| Brain | (−)(2/2) | (−)(2/2) |
| Spinal Cord | (−)(1/1) | (−)(1/1) |
| Lymph Node | (−)(1/1) | (−)(1/1) |
| Skel. Muscle | (−)(1/1) | (−)(1/1) |
| Peripheral Nerve | (−)(1/1) | (−)(1/1) |
| Esophagus | (−)(1/1) | (−)(1/1) |
| Small Bowel | (−)(2/2)(++ serosa) | (−)(2/2)(++ serosa) |
| Stomach | (−;++ serosa)(2/2) | (−;except ++ serosa) (2/2) |
| Colon | (−)(1/1)(++ serosa) | (−;except ++ serosa) (1/1) |
| Bladder | (−)(1/1) | (−)(1/1) |
| Pancreas | (−)(2/2) | (−)(1/2)(+ ducts) (1/2) |
| Salivary Gland | (−)(2/2) | (−)(3/3) |
| Mammary Gland | (−)(1/1) | (−)(1/1) |
| Vaginal Glands | (−)(1/1) | (−)(1/1) |
| Thyroid | (−)(1/1) | (−)(1/1) |
| Parathyroid | (−)(1/1) | (−)(1/1) |
| Ovary | (++ serosa)(1/1) | (++ serosa)(1/1) |
| Cervix | (++ apical gland epith)(1/1) | (++ apical gland epith)(2/2) |
| Uterus | (+ apical endom.; ++serosa)(1/1) | (++ apical endom.; ++ serosa)(1/1) |
| Thymus | (−)(1/1) | (−)(1/1) |
| Trachea | (++ basal epith.; −glands) | (++ apical epith; ++ het glands)(1/1) |
| Tongue | (−)(1/1) | (−)(1/1) |

In order to obtain these results, immunohistochemical analysis was performed on cryostat sections of fresh-frozen tissues, post-fixed in acetone and incubated with primary antibodies at 10 μg/ml except where indicated. Labeling was then performed using affinity-purified goat anti-mouse IgG conjugated to horseradish peroxidase, developed using diaminobenzidine, then treated with hematoxylin followed by osmium tetroxide. (− = no localization; + = moderate; ++ strong)(x/y = X examples of this pattern seen in Y samples tested)(het = heterogeneous)

The reactivity of K1 can also be compared with that of OC125, a previously described antibody (Bast et al., J. Clin. Invest. 68:1331 (1981)). In monkey trachea, for example, the K1 antibody reacts more selectively, than OC125, with the basal less-differentiated epithelial cells. Other differences between the two antibodies can also be observed with respect to the bronchi and endometrium. It should also be noted that K1 reacts strongly with mesothelium.

The presence of antigen epitopes, reactive with K1 or OC125, implies that when these antibodies are used in immunotherapy, these normal tissue sites might be at risk. However, the apical location of such reactive sites in intact epithelia suggests that these sites would not be as accessible to the blood stream which indirectly bathes the basal surfaces of these same cells, as compared to tumor sites. The differential with K1 versus OC125 also suggests a large chemical difference in the nature of the epitopes, and perhaps molecular species, reactive with these antibodies.

In order to further determine the characteristics of the K1 monoclonal antibody and therefore determine its potential usefulness as a diagnostic and therapeutic agent, different cancer cell lines may be examined for reactivity with K1. (see Table II below.) For example, it has been established that various cell lines derived from ovarian, cervical and gastric tumors express the K1 epitope. These cell lines include, for example, OVCAR-2, OVCAR-3, OVCAR-4, 1847, HTB77, HeLa S3, KB, AGs and HTB103 (i.e., Kato III). However, some of these cells lines (for example, 1847, AGS, Kato III) do not react with OC125.

The reaction of K1 with some cells that do not express the OC125 antigen, and the expression of the OC125 antigen on some cells that do not express the K1 antigen, suggest that the two antigens may represent completely different molecules, in addition to representing different epitopes. The existence of cell lines showing homogeneous reaction with K1 suggests that some tumors in vivo may also show a homogeneous reaction with this antibody. A homogeneous reaction with all cells in a tumor would be a great advantage for the success of immunotherapy that could kill every cell in a tumor, rather than just a subpopulation of tumor cells.

TABLE II

Immunofluorescence Localization of K1 and OC125 on Human Cultured Cell Lines

| Cell line | K1 | OC125 |
|---|---|---|
| OVCAR-2 (ovarian Ca) | ++ | ++ het(50%−) |
| OVCAR-3 (ovarian Ca) | ++ het | +++ het |
| OVCAR-4 (ovarian Ca) | ++ het | ++++ het |
| OVCAR-5 (ovarian Ca) | + | − |
| 1847 (ovarian Ca) | +++ | − |
| HTB77(SKOV3)(ovarian Ca) | ++het (30%) | ++het (10%) |
| 2780 (ovarian Ca) | − | − |
| HTB33 (cervical Ca) | − | − |
| HeLa S3 (cervical Ca) | ++ | ++ |
| KB (cervical Ca) | +++ | −(<5%++) |
| AGS (CRL 1739)(gastric Ca) | ++ | − |
| HTB103 (Kato III)(gastric Ca) | ++ | − |
| FEMX (melanoma) | − | − |
| HT-29 (colon Ca) | − | − |
| A431 (epidermoid Ca) | − | +++(<5%) |
| HTB20 (breast Ca) | − | − |
| MDA-MB-468 (breast Ca) | − | − |
| MCF-7 (breast Ca) | − | +++(<1%) |
| DU145 (prostate Ca) | − | ++ het |

Het = heterogenous; (−) = negative; (+ = weakly positive; ++ = moderate; +++ = strong; ++++ = very strong).

Tumors can also be examined for the expression of K1 and OC125 reactivity and thus for the presence of antigens and more specifically, epitopes which react with these two antibodies. (See Tables III and IV below.) K1 reacts, for example, with many ovarian cancers and several other cancers such as carcinomas of the esophagus and cervix. Thus, these results also indicate that K1 and OC125 recognize epitopes that are expressed in different cells and at different levels in various tumors; thus, the two epitopes recognized by these antibodies are probably not the same.

TABLE III

Reactivity of Human Tumors with K1 and OC125
Numbers of Tumors That Show Localization of Either K1 or OC125

| Tumor Type | >95% | −90% | −80% | −70% | −60% | −50% | −40% | −30% | −20% | −15% | −10% | −<5% | −0% | Total # of Tumors |
|---|---|---|---|---|---|---|---|---|---|---|---|---|---|---|
| Ovarian Carcinoma | | | | | | | | | | | | | | |
| K1 | 1 | 2 | 1 | 0 | 4 | 1 | 0 | 1 | 0 | 0 | 0 | 2 | 7 (4 muc.) | 19 |
| OC125 | 8 | 3 | 0 | 0 | 0 | 0 | 0 | 0 | 1 | 1 | 0 | 0 | 6 (4 muc.) | 19 |
| Breast Carcinoma | | | | | | | | | | | | | | |
| K1 | 0 | 0 | 0 | 0 | 0 | 2 | 0 | 0 | 0 | 0 | 1 | 0 | 16 | 19 |
| OC125 | 0 | 0 | 0 | 1 | 1 | 0 | 1 | 1 | 0 | 0 | 0 | 0 | 15 | 19 |
| Colon Carcinoma | | | | | | | | | | | | | | |
| K1 | 0 | 0 | 0 | 1 | 1 | 0 | 0 | 1 | 0 | 0 | 0 | 0 | 20 | 23 |
| OC125 | 0 | 1 | 0 | 0 | 0 | 0 | 0 | 0 | 0 | 0 | 0 | 0 | 22 | 23 |
| Esophageal Carcinoma | | | | | | | | | | | | | | |
| K1 | 0 | 0 | 2 | 0 | 0 | 3 | 0 | 1 | 1 | 0 | 2 | 1 | 5 | 15 |
| OC125 | 0 | 0 | 0 | 0 | 0 | 0 | 0 | 0 | 0 | 0 | 1 | 2 | 12 | 15 |
| Lung Carcinoma | | | | | | | | | | | | | | |
| K1 | 0 | 0 | 0 | 0 | 0 | 0 | 0 | 0 | 0 | 0 | 0 | 0 | 3 | 3 |
| OC125 | 0 | 0 | 0 | 0 | 0 | 0 | 1 | 0 | 1 | 0 | 0 | 0 | 1 | 3 |

| Other Tumors Examined | | |
|---|---|---|
| Tumor Type | K1 Reactivity | OC125 Reactivity |
| Gastric Carcinoma | (−)(4/4) | (−)(1/1) |
| Prostate Carcinoma | (−)(2/2) | (−)(2/2) |
| Cervical Carcinoma | (++)(1/1) | (++)(1/1) |
| Endometrial Carcinoma | (−)(1/1) | (weak het +)(1/1) |

In some tumors, a single pattern was seen in >95% of cells but, because of the limited preservation in cryostat sections, it was not possible to rule out a small % of cells that might show a different intensity.

TABLE IV

Comparison of Percentage and Intensity of Reactive Cells in Individual Tumors for K1 and OC125

| Tumor No. | Type | K1 Reactivity +++ | K1 Reactivity ++ | K1 Reactivity + | K1 Reactivity 0 | OC125 Reactivity +++ | OC125 Reactivity ++ | OC125 Reactivity + | OC125 Reactivity 0 |
|---|---|---|---|---|---|---|---|---|---|
|  | Ovarian Carcinomas |  |  |  |  |  |  |  |  |
| 1 | Ser. Cystad. Ca |  |  |  | >95 | >95 |  |  |  |
| 2 | Ser. Cystad. Ca |  |  |  | >95 | >95 |  |  |  |
| 3 | Ser. Cystad. Ca | 80 | 10 |  | 10 | >95 |  |  |  |
| 4 | Ser. Cystad. Ca | 20 | 40 |  | 40 |  | >95 |  |  |
| 5 | Ser. Cystad. Ca | 10 | 20 |  | 70 | 80 | 10 |  | 10 |
| 6 | Ser. Cystad. Ca | 20 | 40 |  | 40 | >95 |  |  |  |
| 7 | Ser. Cystad. Ca | 40 | 20 |  | 40 | 90 |  |  | 10 |
| 8 | Ser. Cystad. Ca | 20 | 40 | 40 |  | >95 |  |  |  |
| 9 | Ser. Cystad. Ca | 20 | 10 | 20 | 50 |  |  |  | 100 |
| 10 | Met. to Lymph Node | 80 | 10 |  | 10 | >95 |  |  |  |
| 11 | Ser. Cystad. Ca | 30 | 20 |  | 50 | 5 | 40 | 10 | 45 |
| 12 | Ser. Cystad. Ca | 50 | 20 | 10 | 20 | >95 |  |  |  |
|  | Esophageal Carcinomas |  |  |  |  |  |  |  |  |
| 13 | Squamous Ca |  | 20 | 10 | 70 |  |  |  | 100 |
| 14 | Squamous Ca |  | 20 |  | 80 |  |  |  | 100 |
| 15 | Squamous Ca | 60 | 20 |  | 20 |  |  |  | 100 |
| 16 | Squamous Ca |  |  |  | 100 | 0 | 5 | 10 | 85 |
| 17 | Squamous Ca |  |  | 50 | 50 |  |  |  | 100 |
| 18 | Squamous Ca |  |  | 10 | 90 |  |  |  | 100 |
| 19 | Squamous Ca | 50 | 10 | 20 | 20 |  |  |  | >95 |
| 20 | Squamous Ca |  |  | 10 | 90 |  |  |  | 100 |
| 21 | Squamous Ca | 20 | 10 | 20 | 50 |  |  |  | >95 |
| 22 | Squamous Ca | 20 | 10 | 20 | 50 |  |  |  | 100 |

In some tumors, a single pattern was seen in >95% of cells but, because of the limited preservation in cryostat sections, it was not possible to rule out a small % of cells that might show a different intensity.

Furthermore, as manifested by the results using immunofluorescence shown in Table V below, the K1 and OC125-reactive epitopes do not cross-compete for reactivity to the "other" antibody. Additionally, as shown in Tables VI and VII (below), the two antibodies do not cross-compete for binding to cells. These results clearly indicate that K1 and OC125 recognize entirely different epitopes.

TABLE V

Immunofluorescence Detection of Competition of Binding between K1 and OC125

| Rhodamine-Labeled Antibody | Excess Unlabeled Antibody Added | Fluorescence Intensity |
|---|---|---|
| K1-Rhodamine | None | ++ |
| K1-Rhodamine | K1 | 0 |
| K1-Rhodamine | OC125 | ++ |
| OC125-Rhodamine | None | +++ |
| OC125-Rhodamine | K1 | +++ |
| OC125-Rhodamine | OC125 | 0 |

Living OVCAR-3 cells were incubated at 4° C. with rhodamine-labeled direct conjugates of K1 or OC125 antibody at 10 μg/ml alone, or following pre-incubation for 45 min. as co-incubation with unlabeled K1 or OC125 antibodies at 25 μg/ml.

TABLE VI

Radiolabeled Antibody Competition Microtiter Plate Assay on Cells

| Label | Competitor | Unlabeled Antibody Added (μg/ml) | CPM/Well |
|---|---|---|---|
| K1-$^{125}$I | K1 | 0 | 2081 |
|  |  | 0.03 | 1904 |
|  |  | 0.1 | 1413 |
|  |  | 0.3 | 914 |
|  |  | 1.0 | 719 |
|  |  | 3.0 | 367 |
|  |  | 10.0 | 162 |
|  |  | 25.0 | 106 |
| K1-$^{125}$I | OC125 | 0 | 2015 |
|  |  | 3.0 | 2062 |
|  |  | 10.0 | 1993 |
|  |  | 25.0 | 2158 |

OVCAR-3 cells attached to microtiter plates were incubated with or without various concentrations of competitor antibodies, then incubated with $^{125}$I-labeled K1 antibody, washed and counted. Note that K1 antibody competes for $^{125}$I-K1 binding, whereas OC125 antibody does not.

TABLE VII

ELISA Assay of Competition of Live Cell Binding Between K1 and OC125

| Label | Competitor | Competitor Added (μg/ml) | % of Inhibition of Binding |
|---|---|---|---|
| K1-PE | K1 | 0 | 0 |
|  |  | 0.003 | 20 |
|  |  | 0.01 | 48 |
|  |  | 0.1 | 64 |
|  |  | 1.0 | 83 |
|  |  | 10.0 | 98 |
|  |  | 20.0 | 100 |
| K1-PE | OC125 | 0 |  |
|  |  | 1.0 | 0 |
|  |  | 10.0 | 0 |
|  |  | 20.0 | 0 |

OVCAR-3 cells in microtiter plates were incubated with various concentrations of competitor unlabeled antibodies, then K1 antibody covalently coupled to PE (Pseudomonas exotoxin) was added. After washing, the PE hapten was detected using rabbit anti-PE antibody followed by goat anti-rabbit IgG conjugated to horseradish peroxidase. The plate was then developed using ABTS substrate solution, and the optical density was calculated as a percentage of inhibition of maximum binding per well. Note that K1 competes for binding of K1-PE to cells, whereas OC125 does not.

Moreover, unlike OC125, K1 does not react well with the antigen shed into the medium of ovarian carcinoma (OVCAR-3) cultured cells (Table VIII below, FIG. 1). Thus, the K1-reactive antigen does not appear to be shed into the culture medium of OVCAR-3 cells.

Similar results were found in assays of samples of sera from patients with ovarian cancer (FIG. 1). Thus, these results imply that K1-reactive antigen is not shed from ovarian cancer cells, and makes K1 a much better candidate antibody for use in immunotherapy than OC125. Also, it should be noted that purified CA125 antigen does not react with K1. CA125 is the standard antigen which reacts with OC125.

TABLE VIII

Radiolabled Antibody Assay of Culture Supernatant

| Antibody Attached to Well | Dilution of OVCAR-3 Culture Supernatant | CPM/Well |
| --- | --- | --- |
| OC125 | None | 16605 |
|  | 1:3 | 15529 |
|  | 1:9 | 7030 |
|  | 1:27 | 2304 |
|  | 1:81 | 703 |
|  | 1:243 | 392 |
|  | Blank | 302 |
| K1 | None | 371 |
|  | 1:3 | 392 |
|  | 1:9 | 277 |
|  | 1:27 | 263 |
|  | Blank | 318 |

Unlabeled antibody (either K1 or OC125) was attached to microtiter wells. Independent ELISA assays using anti-mouse IgG-peroxidase confirmed that the same amounts of the two antibodies were attached to the wells. OVCAR-3 culture supernatant was then added at various dilutions to these wells, incubated, washed and then $^{125}$I-labeled OC125 antibody was added, incubated and washed. The radioactivity in each well was then measured. Note that (CA125) antigen in the culture supernatant binds to the OC125 antibody on the plate, and this is detected with the radiolabeled OC125 antibody, whereas K1 antibody attached to the plate does not bind any antigen from the supernatant that can be detected by subsequent incubation with labeled OC125.

In addition, quantative enzyme-linked (ELISA) immunosorbent assays of K1 and OC125 binding to OVCAR-3 cells, attached to microtiter plates, show that the addition of K1 and OC125 together produce a signal greater than the value of either antibody alone over a wide concentration range (1–50 $\mu$g/ml) (Table IX below). This fact suggests that the epitopes are sufficiently physically separated enough such that both epitopes can be independently occupied simultaneously.

TABLE IX

ELISA Assay of Additive Binding of Both K1 and OC125

| | OPTICAL DENSITY/WELL × $10^2$ | | | |
| --- | --- | --- | --- | --- |
| Concentration of Antibodies ($\mu$g/ml) | Observed K1 Alone | Observed OC125 Alone | Observed K1 + OC125 | Predicted If Additive |
| 0.3 | 180 | 238 | 390 | 418 |
| 1.0 | 190 | 264 | 407 | 454 |
| 3.0 | 200 | 264 | 409 | 464 |
| 10.0 | 200 | 289 | 421 | 489 |

OVCAR-3 cells were planted in microtiter wells, then incubated with either K1, OC125, or a combination of both at the same individual antibody concentrations shown. The amount of mouse antibody bound to cells was then determined by incubating with goat anti-mouse IgG-peroxidase, and the peroxidase was detected using ABTS substrate. The optical densities shown were measured at 405 nm and were adjusted to the linear range of detection for this system. Note that the quantitative amount of antibody bound per cell is consistent with values expected if both antibodies bind to completely physically separate sites.

Thus, the results of Tables V–IX indicate that K1 reacts with an epitope completely different and physically separate from the OC125 epitope. Furthermore, the differences in the reactive antigen between K1 and OC125 indicate that, in spite of the similarity in their expression in normal tissues and some tumors, the two antigens may represent two entirely different molecules which would have different utility in immunotherapy. CA125, by its property of being shed into the sera of patients, is useful for serum diagnostic purposes, but this same property makes it less useful for immunotherapy because of the neutralization of therapeutic antibody conjugates by this circulating antigen. K1, therefore, represents a much better candidate for immunotherapy because its reactive antigen remains associated with the tumor cell, and allows targeting to the living cell that could mediate selective cell killing by an immunotoxin. If the two antigens are located on completely different molecules, then K1 may be more amenable to the isolation of the gene responsible for antigen expression, yielding a new set of potentially useful reagents.

Previous attempts at isolation of the gene for the CA125 antigen have been unsuccessful, possibly because the antigenic epitope reactive with OC125 antibody has a large amount of carbohydrate as part of its structure. Such carbohydrate additions would be missing in bacterial systems that would have to be used to isolate the gene responsible for CA125 expression. The gene responsible for K1 antigen may not require additional carbohydrate or other post-translational modifications missing in bacterial expression systems and, thus, K1 antibody may be useful for the isolation of the structural gene for the K1-reactive antigen. Expression of such a gene could allow the preparation of pure antigen, the isolation of second generation monoclonal antibodies to different epitopes on the antigen molecule, and the availability of reagents for genetic screening for this antigen gene in the different tumor samples.

Other results examining the properties of the K1 epitope have shown that it can be removed from cells by trypsin treatment. Periodate treatment of cells reduces reactivity with OC125, but slightly increases reactivity with K1. Protein immunoblots of cell extracts, OVCAR culture supernatants and purified CA125 antigen show a high molecular weight (>200 kDaltons) smear on SDS-gel blots that reacts with OC125, but this same region shows no reaction with K1. Thus, it is not yet clear what the exact chemical nature of the K1 antigen is. However, the chemical nature or structure of the K1 antigen is clearly different from CA125.

In view of the above discussion, it is clear that K1 will be useful in the treatment and diagnosis of several types of cancer. The K1 monoclonal antibody recognizes an epitope expressed on the surface of a significant number of common human ovarian, cervical and esophageal tumors, for example. Furthermore, the only significant normal tissue reactivity of this antibody appears to be with the mesothelium of the serosal surfaces of the peritoneum, pleura, and pericardium. This suggests that toxic side-effects of immunotherapy using K1 may be relatively minor. Furthermore, these sites can be evaluated in pre-clinical testing because of the cross-reactivity of this antibody with normal monkey tissues.

More specifically, K1 can be used as a targeting mechanism for directed cancer therapy in the construction of immunotherapeutic agents including, but not limited to, conjugates of K1 with toxins, radionuclides, or chemotherapeutic drugs. Genetic manipulations of the antibody structure can also be undertaken including changing the constant regions of the antibody to human or other species constant regions. Thus, the immunotherapeutic conjugates could therefore contain either the natural form of the antibody or the genetically altered form thereof. Additionally, fusion proteins can be developed utilizing cloned variable region genes for the K1 antibody.

Substitution of human IgG constant regions in the K1 mouse antibody gene, for example, would create a human-mouse chimeric antibody that would be more useful in mediating antibody-directed cell killing in human patients with an intact immune system, a potentially less toxic form of immunotherapy when compared with immunotoxins. Fusion proteins produced in bacterial systems would be much less expensive to manufacture in large amounts.

K1 may also be used as a targeting mechanism for immunodiagnostic assays such as imaging of tumor masses using radioactive imaging techniques. In addition, the expression of the antigen reactive with K1 might prove useful as a diagnostic tool in immunohistopathology for the diagnosis of tumor origins and tissue distributions of metastases. More specifically, immunohistochemical pathologic diagnosis may be made in or using tissue sections (e.g., biopsies) or cytological preparations (e.g., Pap smears, ovarian cancer effusions, etc.). Other diagnostic uses might include locating tumors using radioactive labeling of K1 antibody on a macroscopic scale at the time of surgical exploration.

The present invention can be illustrated by the use of the following non-limiting examples.

EXAMPLE I

Production of the K1 Antibody

The human tumor cell lines OVCAR-2, 3, 4, and 5, KB, AGS, MCF-7, HT-29, MDA-MB-469, DU145, HTB20, and HTB33 have been previously described (Hay et al., *American Type Culture Collection Catalog Of Cell Lines and Hybridomas*, 6th Ed. (1988)). Mice were tolerized to normal human kidney membranes (Matthew et al., *J. Immunol. Methods* 100:73–82 (1987)). They were then immunized with OVCAR-3 cells (Willingham et al., *Proc. Natl. Acad. Sci. U.S.A.* 84:2474–78 (1987)). However, the cultured cells were treated with periodate. This periodate treatment was performed to link anti-mouse IgG to the surface of these cells in a strategy to improve targeting of immunizing antigens to mouse antibody-bearing lymphocytes. Spleens from immunized mice were removed and the suspended spleen cells were selected for reactivity to OVCAR-3 cells prior to fusion by a panning method. The selected spleen cells were fused with AG8 mouse myeloma cells, and the resulting clones were screened two weeks later employing the ScreenFast (Life Technologies, Ind., Gaithersburg, Md.) large scale screening chamber using rhodamine indirect immunofluorescence on living OVCAR-3 cells. Selected clones were secondarily screened using peroxidase immunohistochemistry on cryostat sections of human tumors and normal tissues. One clone, K1, was selected that reacted with ovarian cystadenocarcinomas and did not react with normal liver, kidney, colon, small bowel, bone marrow, cerebellum, lung, heart or cerebral cortex. This clone was originally an IgM antibody clone, that was converted to an IgG variant following subcloning using a panning-isotype switching method (Chang et al. (in preparation)).

After re-cloning, the resultant isotype of the K1 hybridoma was determined to be mouse $IgG_{1k}$. Antibody was produced from the IgG clone using either ascites production in mice or harvests of culture supernatants, and purified using a protein A FPLC affinity column.

EXAMPLE II

Use of Peroxidase Immunohistochemistry To Demonstrate The Distribution Of The Epitope Reactive With The K1 Antibody Samples of fresh-frozen human and Cynomologous monkey normal tissues, as well as human tumor samples, were cryostat sectioned, mounted on glass coverslips and processed for peroxidase immunohistochemistry as previously described (Willingham, *FOCUS* 12:62–67 (1990)) using K1 as the primary antibody. The localization of reactive antigen in various tissues was detected using the peroxidase substrate reaction with diaminobenzidine. This example demonstrated the localization of reactive antigen in the lining mesothelium of the peritoneum, pleura, and pericardium in both human and monkey tissues. Reactive antigen was also found in lesser amounts in the epithelia of the trachea, tonsil and Fallopian tube. In human tumor samples, reaction with K1 was found in tumors derived from ovary, esophagus, and cervix and to a lesser extent in tumors derived from breast and colon.

EXAMPLE III

Examination of Different Cancer Cell Lines For Reactivity With the K1 Antibody Using Immunofluorescence Living human cultured tumor cell lines were washed free of culture medium and incubated at 4° C. with monoclonal antibody K1 (1 µg/ml) in buffered saline. After washing, the bound antibody was detected by incubating cells in rhodamine-conjugated goat anti-mouse IgG antibody, then fixed in formaldehyde and viewed using an epifluorescence microscope as previously described (Willingham, *FOCUS* 12:62–67 (1990)). Cells showing strong reactivity with K1 antibody included, for example, KB, HeLa S3, OVCAR-3, AGS, Kato III, and 1847 cells.

EXAMPLE IV

Direct Competition Assays For K1 Epitope Reactivity

Living OVCAR-3 cells were incubated at 4° C. with rhodamine-labeled direct conjugates of antibody K1 or antibody OC125 (10 µg/ml) in the presence or absence of excess unlabeled competitor K1 or OC125 antibody (25 µg/ml), having preincubated the same cells with the same unlabeled competitor antibody prior to this incubation. After this step, the cells were washed, fixed in formaldehyde and viewed using epifluorescence microscopy. K1-rhodamine showed strong labeling in the absence of competitor antibody or in the presence of OC125 as a competitor, but no labeling when K1 was used as a competitor. Conversely, OC125 showed strong labeling in the absence of competitor or in the presence of excess K1 competitor antibody, but no labeling when OC125 was used as a competitor. This result indicates one example of the lack of cross-reactivity between the OC125 and K1 epitopes.

We claim:

1. A hybridoma which produces a monoclonal antibody specific for a cell surface antigen, wherein said antigen is characterized by expression on normal primate tissue, malignant human cultured cell lines and human tumors; is not shed into culture media or plasma, and wherein binding of the monoclonal antibody to the antigen is inhibited in the presence of a monoclonal antibody secreted by ATCC Accession No. HB 10570.

2. A monoclonal antibody specific for a cell surface antigen wherein said antigen is characterized by expression on normal primate tissue, malignant human cultured cell lines, and human tumors, is not shed into plasma; wherein said monoclonal antibody is of the class IgG1, and wherein binding of the monoclonal antibody to the antigen is inhibited in the presence of a monoclonal antibody secreted by ATCC Accession No. HB 10507.

3. The hybridoma of claim 1 wherein the malignant human cultured cell line is selected from the group consisting of OVCAR-2, OVCAR-3, OVCAR-4, 1847, HTB77, HeLa S3, KB, AGS and HTB103.

4. The monoclonal antibody of claim 2 wherein the malignant human cultured cell line is selected from the group consisting of OVCAR-2, OVCAR-3, OVCAR-4, 1847, HTB77, HeLa S3, KB, AGS and HTB103.

5. The hybridoma of claim 1 wherein said human tumor is derived from an ovarian carcinoma, an esophageal carcinoma or a cervical carcinoma.

6. The monoclonal antibody of claim 2 wherein said human tumor is derived from an ovarian carcinoma, an esophageal carcinoma or a cervical carcinoma.

7. The hybridoma of claim 1 wherein said normal primate tissue is mesothelium.

8. The monoclonal antibody of claim 2 wherein said normal primate tissue is mesothelium.

9. The hybridoma cell line of the accession number ATCC HB 10570.

10. A monoclonal antibody produced by the hybridoma of claim 1.

11. The monoclonal antibody of claim 2 wherein said antibody is produced by the hybridoma having ATCC Accession No. HB 10570.

12. A hybridoma deposited with the American Type Culture Collection having Accession No. HB 10570 which produces an IgG class monoclonal antibody that specifically binds a non-shedding cell surface antigen found on:
 1) the apical surface of the normal mesothelium, tracheal epithelium, tonsillar epithelium and epithelium of the fallopian tube,
 2) human cultured cell lines selected from the group consisting of OVCAR-2, OVCAR-3, OVCAR-4, 1847, HTB77, HeLa S3, AGS and HTB103, and
 3) human tumors derived from an ovarian carcinoma, an esophageal carcinoma or a cervical carcinoma.

13. The monoclonal antibody produced by the hybridoma of claim 12.

* * * * *